(12) United States Patent
Kishan et al.

(10) Patent No.: US 11,589,903 B2
(45) Date of Patent: Feb. 28, 2023

(54) SPINAL FIXATION DEVICE

(71) Applicant: K2M, Inc., Leesburg, VA (US)

(72) Inventors: Shyam Kishan, Indianapolis, IN (US); Michael Barrus, Redondo Beach, CA (US)

(73) Assignee: K2M, Inc., Leesburg, VA (US)

( * ) Notice: Subject to any disclaimer, the term of this patent is extended or adjusted under 35 U.S.C. 154(b) by 98 days.

(21) Appl. No.: 17/168,673

(22) Filed: Feb. 5, 2021

(65) Prior Publication Data

US 2021/0153910 A1    May 27, 2021

Related U.S. Application Data

(62) Division of application No. 14/675,820, filed on Apr. 1, 2015, now Pat. No. 10,918,419.

(60) Provisional application No. 61/973,405, filed on Apr. 1, 2014.

(51) Int. Cl.
*A61B 17/70*    (2006.01)

(52) U.S. Cl.
CPC ................ *A61B 17/7037* (2013.01)

(58) Field of Classification Search
CPC ............................ A61B 17/70–7046
See application file for complete search history.

(56) References Cited

U.S. PATENT DOCUMENTS

| | | |
|---|---|---|
| 4,950,269 A | 8/1990 | Gaines, Jr. |
| 5,683,392 A | 11/1997 | Richelsoph et al. |
| 6,010,503 A | 1/2000 | Richelsoph et al. |
| 6,736,820 B2 | 5/2004 | Biedermann et al. |
| 7,090,674 B2 | 8/2006 | Doubler et al. |
| 7,118,303 B2 | 10/2006 | Doubler et al. |
| 7,334,961 B2 | 2/2008 | Doubler et al. |
| 7,335,201 B2 | 2/2008 | Doubler et al. |
| 7,445,627 B2 | 11/2008 | Hawkes et al. |
| 7,658,582 B2 | 2/2010 | Doubler et al. |
| 7,678,136 B2 | 3/2010 | Doubler et al. |
| 7,785,354 B2 | 8/2010 | Biedermann et al. |
| 3,038,701 A1 | 10/2011 | Rock et al. |
| 8,092,503 B2* | 1/2012 | Felix ............... A61B 17/88 606/267 |
| 8,361,122 B2 | 1/2013 | Barrus et al. |
| 8,409,260 B2 | 4/2013 | Biedermann et al. |
| 8,506,600 B2 | 8/2013 | Carbone et al. |
| 8,672,944 B2 | 3/2014 | Boachie-Adjei et al. |
| 8,864,803 B2 | 10/2014 | Biedermann et al. |
| 8,870,930 B2 | 10/2014 | Carbone et al. |

(Continued)

*Primary Examiner* — Eduardo C Robert
*Assistant Examiner* — Steven J Cotroneo
(74) *Attorney, Agent, or Firm* — Lerner, David, Littenberg, Krumholz & Mentlik, LLP

(57) ABSTRACT

A spinal fixation device includes an inner housing, an outer housing, a screw, and a pivot inhibitor. The outer housing is circumferentially disposed around at least a portion of the inner housing, wherein the outer and inner housings are translatable relative to one another to cause transitioning of the spinal fixation device between a locked configuration and an unlocked configuration. The screw including a screw head pivotably coupled to a lower portion of the inner housing and a shaft extending from the screw head. The pivot inhibitor is coupled to one of the inner housing or screw, such that pivoting of the inner housing about the screw head is inhibited in a direction of the pivot inhibitor.

18 Claims, 13 Drawing Sheets

(56) References Cited

U.S. PATENT DOCUMENTS

| | | |
|---|---|---|
| 8,945,194 B2 | 2/2015 | Biedermann et al. |
| 9,005,259 B2 | 4/2015 | Biedermann et al. |
| 9,084,634 B1 | 7/2015 | Lab et al. |
| 11,234,745 B2* | 2/2022 | Jackson .............. A61B 17/8605 |
| 2003/0055426 A1 | 3/2003 | Carbone et al. |
| 2004/0147937 A1 | 7/2004 | Dunbar et al. |
| 2004/0158247 A1 | 8/2004 | Sitiso et al. |
| 2005/0049589 A1 | 3/2005 | Jackson |
| 2005/0053423 A1 | 3/2005 | Doubler et al. |
| 2005/0149048 A1 | 7/2005 | Leport et al. |
| 2006/0089644 A1* | 4/2006 | Felix .................. A61B 17/7037 606/270 |
| 2006/0200132 A1 | 9/2006 | Chao et al. |
| 2006/0276792 A1 | 12/2006 | Ensign et al. |
| 2007/0090238 A1* | 4/2007 | Justis ................. A61B 17/7038 248/181.1 |
| 2007/0093817 A1* | 4/2007 | Barrus ................ A61B 17/861 606/264 |
| 2007/0161996 A1 | 7/2007 | Biedermann et al. |
| 2007/0286703 A1 | 12/2007 | Doubler et al. |
| 2008/0027432 A1* | 1/2008 | Strauss .............. A61B 17/7037 606/279 |
| 2008/0243193 A1 | 10/2008 | Ensign et al. |
| 2009/0105716 A1* | 4/2009 | Barrus .............. A61B 17/7032 606/103 |
| 2009/0105769 A1* | 4/2009 | Rock .................. A61B 17/7038 606/301 |
| 2009/0198280 A1* | 8/2009 | Spratt ................ A61B 17/7037 606/267 |
| 2010/0145394 A1* | 6/2010 | Harvey ............. A61B 17/7049 606/305 |
| 2010/0204735 A1* | 8/2010 | Gephart ............ A61B 17/7082 606/279 |
| 2012/0185003 A1* | 7/2012 | Biedermann ...... A61B 17/7032 606/328 |
| 2012/0232598 A1* | 9/2012 | Hestad .............. A61B 17/7037 29/446 |
| 2013/0110178 A1* | 5/2013 | Biedermann ...... A61B 17/7038 606/305 |
| 2013/0144342 A1* | 6/2013 | Strauss ............... A61B 17/70 606/279 |

* cited by examiner

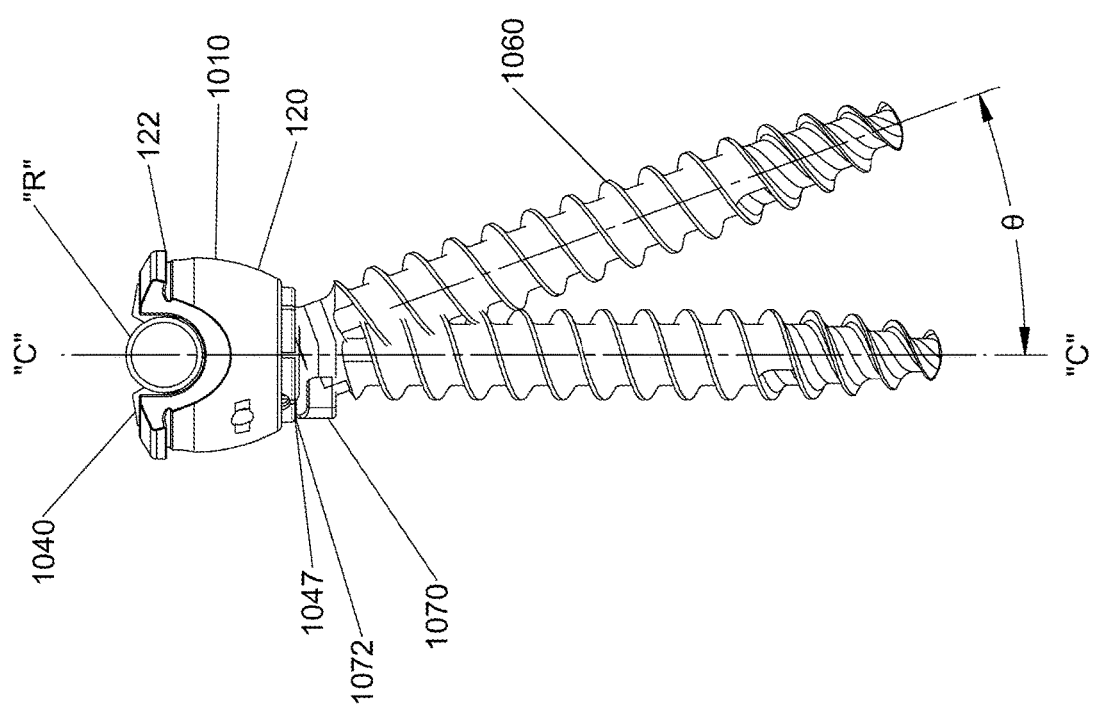

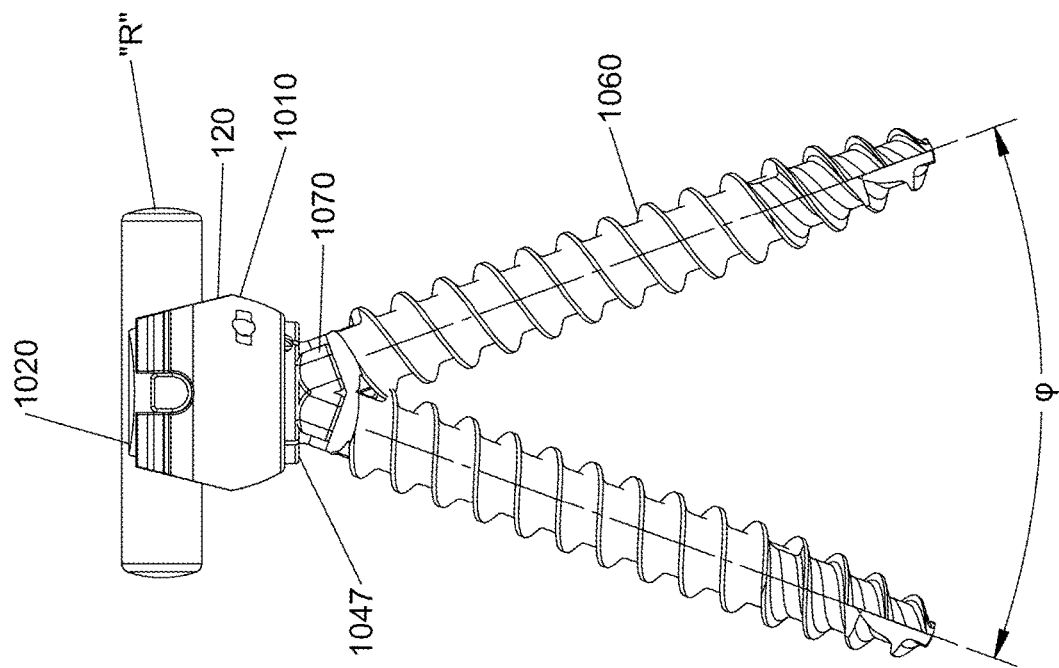

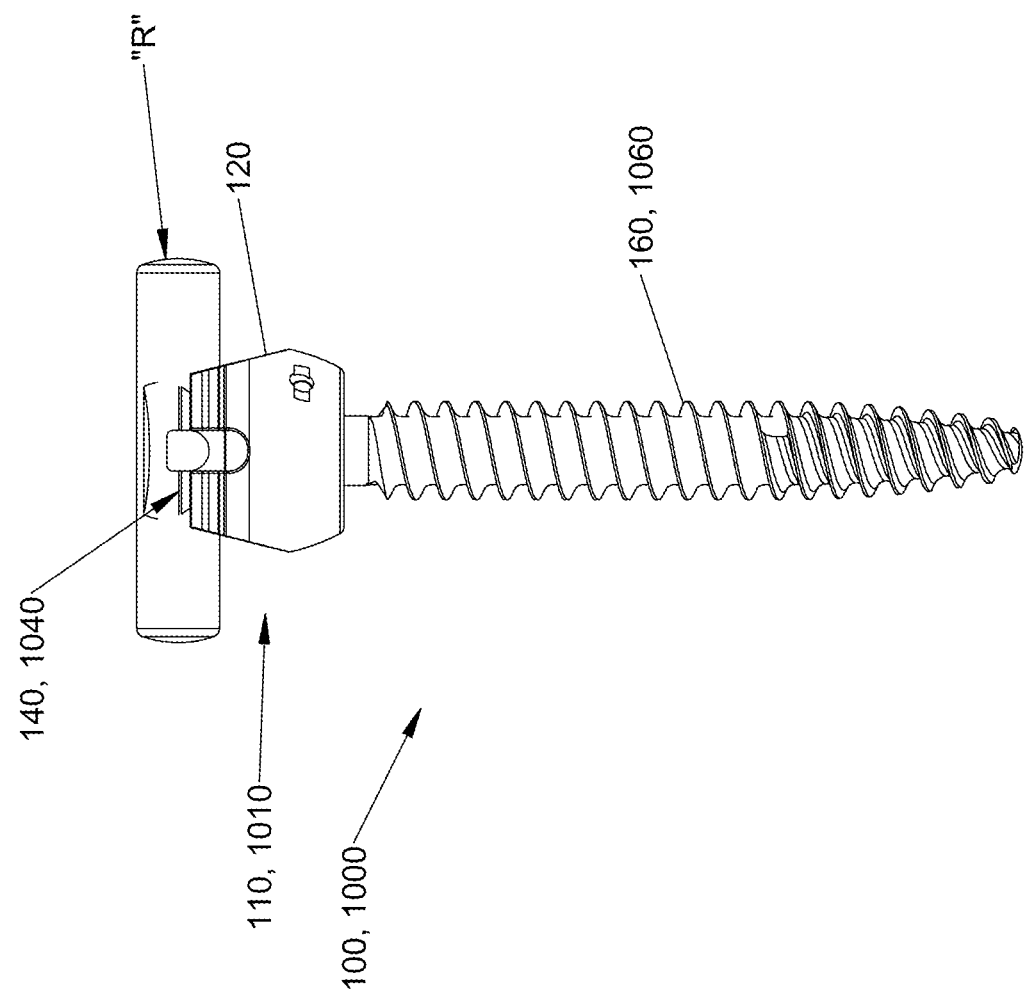

SPINAL FIXATION DEVICE

CROSS-REFERENCE TO RELATED APPLICATIONS

The present application is a divisional of U.S. patent application Ser. No. 14/675,820, filed on Apr. 1, 2015, which claims the benefit of U.S. Provisional Application Ser. No. 61/973,405, filed on Apr. 1, 2014, the disclosures of which are each hereby incorporated herein by reference.

BACKGROUND

Technical Field

The present disclosure relates to a spinal fixation device, and more particularly, to a spinal fixation device that is connectable to a spinal rod used in a spinal construct and a method of use therefor.

Background of Related Art

The spine or spinal column is a complex system of bones and connective tissues that provide support for the human body and protection for the spinal cord and nerves. The adult spine is comprised of an upper portion and a lower portion. The upper portion contains twenty-four discrete vertebrae, which are subdivided into three areas including seven cervical vertebrae, twelve thoracic vertebrae, and five lumbar vertebrae. The lower portion is comprised of the sacral and coccygeal bones. The cylindrical shaped bones, called vertebrae or vertebral bodies, progressively increase in size from the upper portion downwards to the lower portion.

An intervertebral disc, along with two posterior facet joints, cushion and dampen the various translational and rotational forces exerted upon the spinal column. The intervertebral disc is a spacer located between two adjacent vertebral bodies. The facets provide stability to the posterior portion of adjacent vertebrae. The spinal cord is housed in the canal of the vertebral bodies. It is protected posteriorly by the lamina. The lamina is a curved surface with three main protrusions. Two transverse processes extend laterally from the lamina, while the spinous process extends caudally and posteriorly. The vertebral bodies and lamina are connected by a bone bridge called the pedicle.

The spine is a flexible structure capable of a large range of motion. There are various disorders, diseases, and types of injury, which restrict the range of motion of the spine or interfere with important elements of the nervous system. The problems include, but are not limited to, scoliosis, kyphosis, excessive lordosis, spondylolisthesis, slipped or ruptured discs, degenerative disc disease, vertebral body fracture, and tumors. Persons suffering from any of the above conditions typically experience extreme or debilitating pain and often times diminished nerve function. These conditions and their treatments can be further complicated if the patient is suffering from osteoporosis, or bone tissue thinning and loss of bone density.

Spinal fixation apparatuses are widely employed in surgical processes for correcting spinal injuries and diseases that require the imposition and/or maintenance of corrective forces on the spine in order to return the spine to its normal condition. In order to facilitate stabilizing the spine and keeping the interbody in position, other implants are commonly employed, such as bone screws and rods. One type of spinal construct may include, for example, one or more spinal rods that can be placed parallel to the spine with fixation devices (e.g., hooks, screws, or plates) interconnected between the spinal rods at selected portions of the spine. The spinal rods can be connected to each other via cross-connecting members to provide a more rigid support and alignment system.

Where a rod is used as a support and stabilizing member, commonly a series of two or more screws are inserted into two or more vertebrae. A rod is then placed within or coupled to the heads of the screws, or is placed within a connecting device that links the rod and a screw head, and the connections are tightened. In this way, a rigid supporting structure is fixed to the vertebrae, with the rod providing the support that maintains and/or promotes correction of the vertebral malformation or injury.

Some devices allow one or more degrees of freedom between a fastening portion or member and a receiving portion or member, thereby reducing the required precision of placement of the fixation device and/or providing increased flexibility in assembling a rod construct. A head portion of the fixation device may be multi-axially or polyaxially positionable. The head can be positioned so as to easily receive the rod, limiting or removing much of the positioning difficulty inherent in prior devices. However, such devices provide a single maximum angle between the fastening portion and the receiving portion for every relative orientation of those parts. Other devices have made possible a larger maximum angle between the fastening portion and the receiving portion when the fastening portion occupies one position with respect to the receiving portion, but allows only a smaller maximum angle when the fastening portion occupies any other position with respect to the fastening portion.

Usually, the surgeon attaches the spinal fixation devices to the spine in the appropriate anatomical positions and then attaches the spinal rod to the fixation devices. In conjunction with assembling the rod construct, the surgeon manipulates the spinal column and/or individual vertebrae to provide the desired treatment for the spinal defect. Subsequently, the spinal rod and fixation devices are locked in a desired arrangement.

While the aforementioned spinal fixation devices may be suitable for the above uses, there exists a need for a directionally controllable fixation device that limits the angle between the fastening portion and the receiving portion in only a section of the polyaxial fixation device to facilitate the manipulation of the spine and reduction of spinal deformities.

SUMMARY

The present disclosure is directed to a spinal fixation device including an inner housing, an outer housing circumferentially disposed around at least a portion of the inner housing, a screw, and a pivot inhibitor. Further, the outer and inner housings are translatable relative to one another to transition the spinal fixation device between a locked configuration and an unlocked configuration. The screw includes a screw head pivotably coupled to a lower portion of the inner housing, and a shaft extending from the screw head. The pivot inhibitor is coupled to one of the inner housing or the screw, and inhibits pivoting of the screw with respect to the inner housing in a direction of the pivot inhibitor.

In an embodiment, the inner housing further includes a distal surface transverse to a longitudinal axis of the inner housing, and the pivot inhibitor is disposed on the distal surface. The pivot inhibitor may extend distally into a longitudinal throughhole of the outer housing. The pivot inhibitor may extend distally of an equator of the screw head, where the equator is transverse to a longitudinal axis of the shaft. The pivot inhibitor may be monolithically formed with the inner housing. The distal surface of the inner housing may further define a circumference, and the pivot inhibitor may be disposed along a portion of the circumference. The pivot inhibitor may be disposed along approximately one-quarter of the circumference of the distal surface of the inner housing. The pivot inhibitor may further include a distal surface, and the screw may further include a neck disposed between the screw head and the shaft. The distal surface of the pivot inhibitor may abut the neck of the screw when a longitudinal axis of the shaft is coaxial with the longitudinal axis of the inner housing. The pivot inhibitor may further define an inner surface contoured to receive the screw head of the screw.

In yet another embodiment, the screw may further include a neck disposed between the screw head and the shaft, and the neck defines an outer surface, where the pivot inhibitor is disposed on the outer surface. The pivot inhibitor may extend radially outward from the outer surface of the neck. The pivot inhibitor may extend past the screw head and the shaft. The pivot inhibitor may be monolithically formed with the screw. The pivot inhibitor may further include a top surface and the inner housing may further include a distal surface. The top surface may abut the distal surface when a longitudinal axis of the shaft is coaxial with a longitudinal axis of the inner housing. The distal surface of the inner housing may be transverse to the longitudinal axis of the inner housing.

In a further embodiment, a method of spinal fixation is provided. The method includes selectively rotating an inner housing and an outer housing about a longitudinal axis of a screw. The inner and outer housings are rotatably and pivotably coupled to a screw head of the screw. The method additionally includes selectively pivoting the screw with respect to the inner and outer housings about the screw head. The screw is inhibited from pivoting in the direction of a pivot inhibitor coupled to one of the inner housing or the screw. The method further includes inserting a shaft of the screw into the bone, and selectively rotating and pivoting the inner and outer housings into a final position. The method next provides that the outer housing is translated towards the inner housing thereby fixing the spinal rod into the slot and inhibiting any further rotation or pivoting.

In a further embodiment, a kit for spinal fixation is provided. The kit includes at least one spinal fixation device and at least one spinal rod. Each spinal fixation device includes an inner housing, an outer housing, a screw, and a pivot inhibitor. The screw is pivotably coupled to the inner housing, and the pivot inhibitor is coupled to one of the inner housing or the screw. The pivot inhibitor inhibits pivoting of the screw relative to the inner housing in a direction of the pivot inhibitor.

BRIEF DESCRIPTION OF THE DRAWINGS

The foregoing and other features of the present disclosure will become apparent to one skilled in the art to which the present disclosure relates upon consideration of the following description of the disclosure with reference to the accompanying drawings, wherein:

FIG. 11 is a front view of the spinal fixation device of FIG. 7 with a spinal rod, depicting a medial-lateral angle θ;

FIG. 12 is a side view of the spinal fixation device and spinal rod of FIG. 11, depicting a cranial-caudal angle φ;

FIG. 14A is a side view of the spinal fixation device of FIGS. 1 and 7, in an unlocked configuration, and a spinal rod.

DETAILED DESCRIPTION OF EMBODIMENTS

Figure 1:
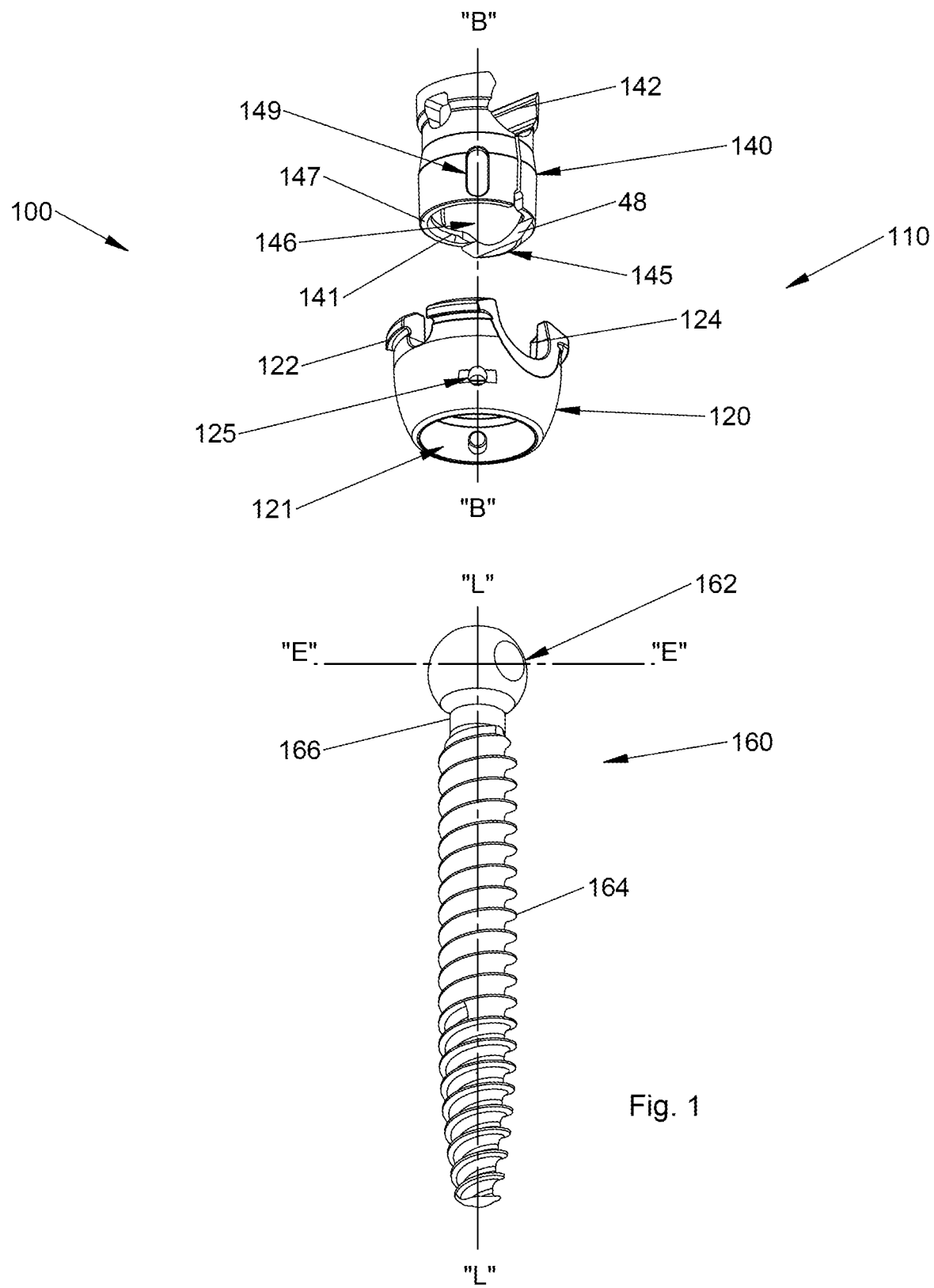
FIG. 1 is a front perspective view, with parts separated, of a spinal fixation device in accordance with an embodiment of the present disclosure.

Embodiments of the present disclosure will now be described in detail with reference to the drawings, in which like reference numerals designate identical or corresponding elements in each of the several views. As is understood in the art, the term "distal," will refer to that portion of the instrument, apparatus, device or component thereof which is farther from the user while, the term "proximal," will refer to that portion of the instrument, apparatus, device or component thereof which is closer to the user. In addition, the term "cephalad" is understood to indicate a direction toward a patient's head, while the term "caudad" indicates a direction toward the patient's feet. Further still, the term "medial" is understood to indicate a direction toward the middle of the body of the patient, while the term "lateral" indicates a direction toward a side of the body of the patient, i.e., away from the middle of the body of the patient. The term "posterior" is understood to indicate a direction toward the patient's back, while the term "anterior" indicates a direction toward the patient's front. In the following description, well-known functions or constructions are not described in detail to avoid obscuring the present disclosure in unnecessary detail.

Figure 2:
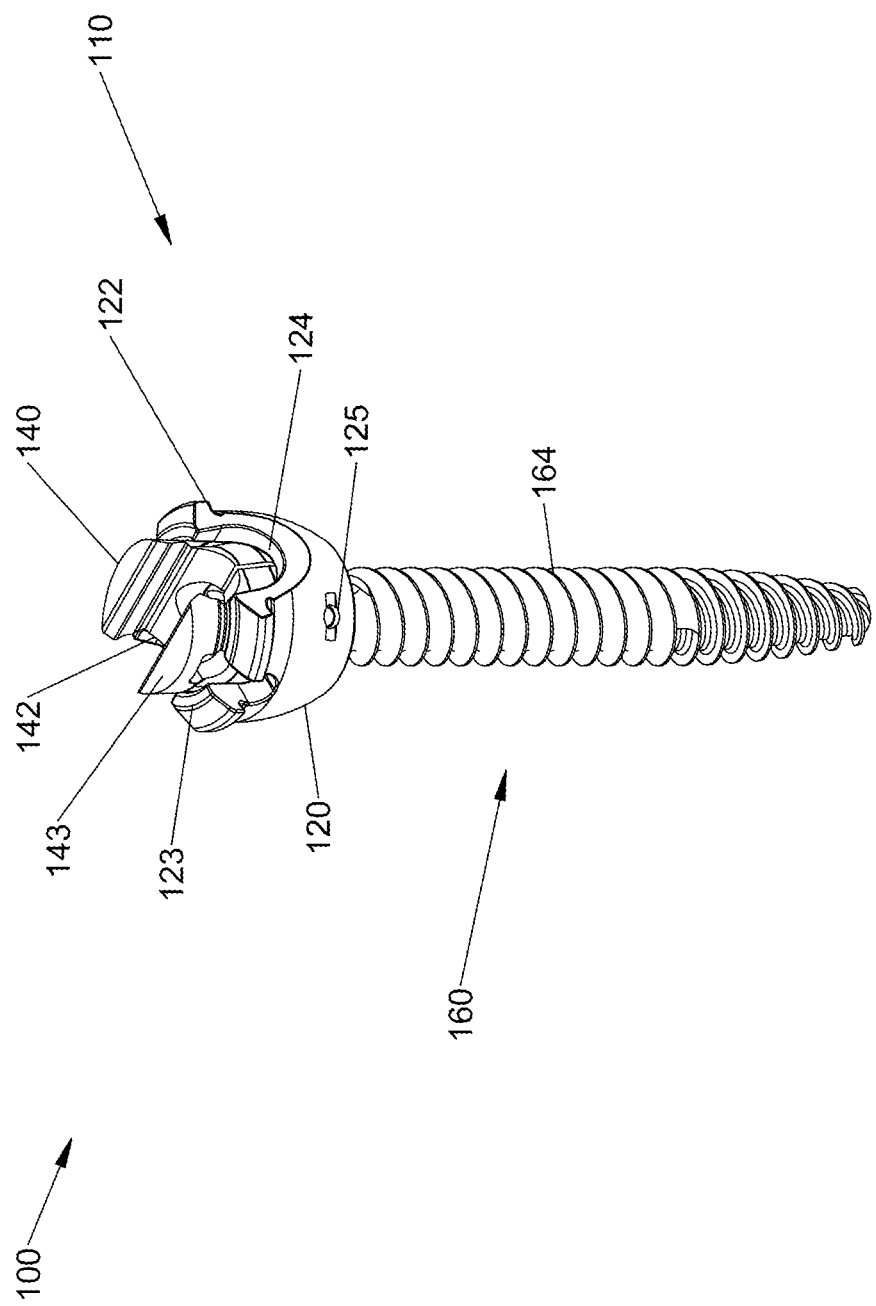
FIG. 2 is a front perspective view, with parts assembled, of the spinal fixation device of FIG. 1.

With reference to FIGS. 1 and 2, an embodiment of the present disclosure is shown generally as spinal fixation device 100 including a dual layered housing 110 and a screw shaft 160. Spinal fixation device 100 is adapted to cooperatively couple with a spinal rod "R" (FIG. 6), which is configured and dimensioned to be selectively and releasably secured to spinal fixation device 100 as discussed below. It is envisioned that spinal rod "R" may be made of a bio-compatible material such as Titanium (Ti-CP) and its alloys (e.g., Ti-6Al-4V), Cobalt-Chrome Alloy (CoCr), Stainless Steel (SS), or polyetheretherketone (PEEK).

Screw shaft 160 may include a spherical screw head 162, a neck 166, and a threaded distal portion 164 extending therefrom, where the threaded distal portion 164 is adapted to penetrate bone thereby securing screw shaft 160 therein. It is envisioned that when screw shaft 160 is coupled to dual layered housing 110, spherical screw head 162 is rotatably and pivotably coupled to dual layered housing 110, such that dual layered housing 110 may rotate about a longitudinal axis "L" of screw shaft 160, and may further pivot about spherical screw head 162 relative to longitudinal axis "L", as discussed below in further detail. It should be appreciated that once the threaded distal portion 164 is affixed to bone and the dual layered housing 110 is coupled to the screw head 162, spinal rod "R" may be consequently secured in dual layered housing 110, thus affixing spinal rod "R" to the bone.

Dual layered housing 110 includes an outer housing 120 and an inner housing 140, both of which contain a throughhole 121, 141 respectively. It should be appreciated that dual layered housing 110 provides a taper lock configuration, such that at least a portion of an inner surface of outer housing 120 is capable of sliding over a portion of an outer surface of inner housing 140 in upward and downward directions along a longitudinal axis "B" of dual layered housing 110. It is envisioned that a locking instrument may be used to insert, reduce, and lock spinal rod "R" securely in place within spinal fixation device 100, while a complementarily designed unlocking instrument may be used to selectively unlock spinal rod "R" from spinal fixation device 100. An additional instrument may be utilized to partially lock dual layered housing 110. Examples of instruments for locking, unlocking, and partially locking the spinal fixation device 100 are disclosed in U.S. Pat. No. 8,361,122, which is hereby incorporated by reference in its entirety. When partially locked, spinal rod "R" is retained in spinal fixation device 100, and the rotational and pivotal position of bone screw 160 with respect to dual layered housing 110 is maintained, while permitting further adjustments to be made. It is envisioned that a separate instrument may lock, unlock, or partially lock dual layered housing 110, a single instrument may lock, unlock, or partially lock dual layered housing 110, or any combination of the above.

By using the locking instrument, outer housing 120 may be driven upward along longitudinal axis "B" towards inner housing 140, thereby transitioning dual layered housing 110 from an unlocked configuration (FIG. 14A) to a locked configuration (FIG. 14B), as discussed more fully herein. Outer housing 120 may include a receiving element configured to facilitate grasping of spinal fixation device 100 by the locking, unlocking, and/or partial locking instrument (not shown). The receiving element may be a proximally located annular flange 122 extending radially from an upper portion of an outer surface of outer housing 120. Locked, unlocked, and partial locked configuration of dual layered housing 110 is shown and described in U.S. Pat. No. 8,361,122.

Figure 4:
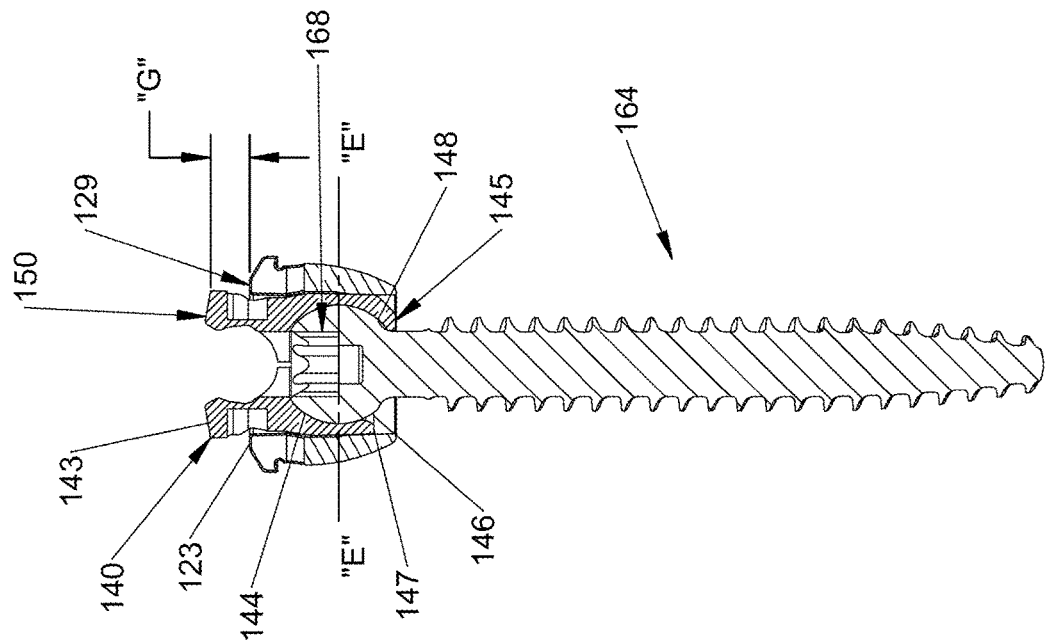
FIG. 4 is a cross-sectional view, taken along section line 4-4 of FIG. 3, of the spinal fixation device of FIG. 1.
Figure 3:
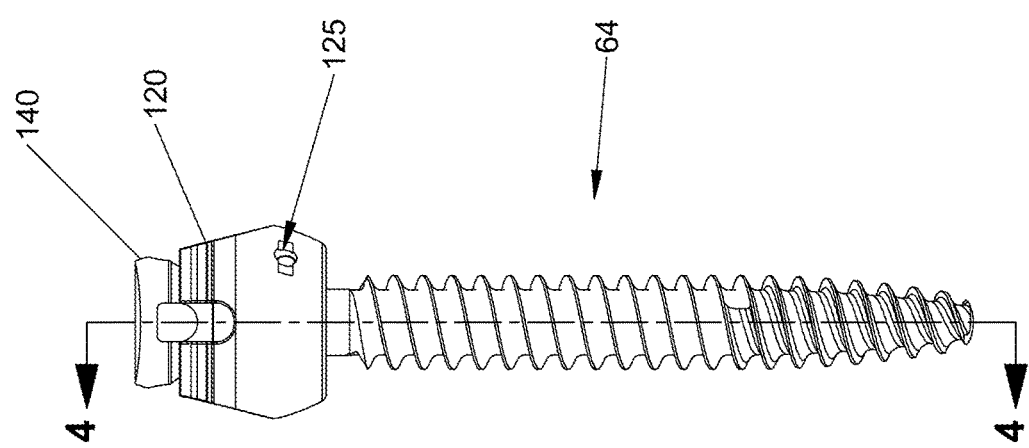
FIG. 3 is a side view of the spinal fixation device of FIG. 1.

Inner housing 140 further defines a screw head articulation recess 144 in a lower portion thereof (FIG. 4). The interior surface of the screw head articulation recess 144 has a complementary surface configuration to the generally spherical shape of spherical screw head 162 to facilitate rotational and pivotal articulation of spherical screw head 162 within the screw head articulation recess 144. The lower-most portion of inner housing 140 defines a screw shaft exit portal 146 that is sized small enough to retain the spherical screw head 162 within the screw head articulation recess 144, but that is large enough to allow multi-directional movement of spherical screw head 162. Multi-directional movement of screw head 162 results in complementary multi-directional movement of the threaded distal portion 164 which extends distally from the inner housing 140. It is envisioned that screw shaft exit portal 146 may be generally circular and further define a distal surface 147 along a circumference thereof, where a space is further defined between the distal surface 147 and the threaded distal portion 164 of screw shaft 160.

It is further contemplated that spinal fixation device 100 may be configured as a uni-planar taper lock screw. In such an embodiment, spherical screw head 162, and thus screw shaft 160, are configured for uni-planar pivoting with respect to inner housing 140. The uni-planar pivotal relationship of the spherical screw head 162 with respect to the dual layered housing 110 facilitates spinal rod positioning and attachment. The restriction of pivoting in any other plane may serve to facilitate the manipulation and realignment of the spine. Failure to limit all other pivoting during the manipulation of the spine could result in the dual layered housing 110 pivoting over to one side or the other relative to the longitudinal axis "L" of the screw shaft 160. The uni-planar configuration effectively restricts movement to a single plane and thus avoids any undesirable multi-planar movement during manipulation of the spine. Further detail regarding uni-planar taper lock screws are shown and described in U.S. Pat. Nos. 8,038,701 and 8,672,944, the entire contents of which are incorporated herein by reference.

Inner housing 140 may further include a contact surface 145 extending distally from the distal surface 147 along a portion of the circumference of the distal surface 147 (FIGS. 1 and 4). Contact surface 145 engages neck 166 to limit pivoting of screw 160. It is envisioned that contact surface 145 may extend along approximately one-quarter of the circumference of the distal surface 147. It should be appreciated that with inner housing 140 coupled to outer housing 120, contact surface 145 extends distally into throughhole 121 of outer housing 120. Further, contact surface 145 may maintain a generally arcuate inner surface 148, such that the inner surface 148 is complementary to the generally spherical shape of spherical screw head 162. It is envisioned that contact surface 145 may be monolithically formed with inner housing 140, or may be coupled thereto by any means known in the art.

With outer housing 120, inner housing 140, and screw shaft 160 coupled together (FIG. 4), the distal surface 147 of inner housing 140 extends distally of a plane E-E that is transverse to longitudinal axis "L" of screw shaft 160 (FIG. 1). It should be appreciated that plane E-E defines an equator of spherical screw head 162. It is envisioned that the distal surface 147 may be positioned distal of plane "E-E" but proximal of the neck 166 of screw shaft 160. In one embodiment, distal surface 147 is equally spaced between plane "E-E" and neck 166 of screw shaft 160. It is further envisioned that contact surface 145 may extend from the distal surface 147 such that a distal end of contact surface 145 is in approximation with neck 166.

It is envisioned that screw shaft 160 and dual layered housing 110 of spinal fixation device 100 may be formed from any suitable biocompatible metal (e.g., stainless steel, titanium, titanium alloys, cobalt chrome, etc.). It is further envisioned that spherical screw head 162, neck 166, and threaded distal portion 164 may be monolithically formed, or alternatively, joined by any means known in the art. Further, outer and inner housings 120, 140 may be joined together through any suitable means known in the art, for example, outer and inner housings 120, 140 may be pinned together using a pin 125 which extends radially inward from outer housing 140. Pin 125 may be adapted to ride in a slot 149 of inner housing 140, wherein pin 125 and slot 140 may further serve to maintain rotational alignment between the outer and inner housings 120, 140 while allowing relative sliding motion therebetween.

Figure 14B:
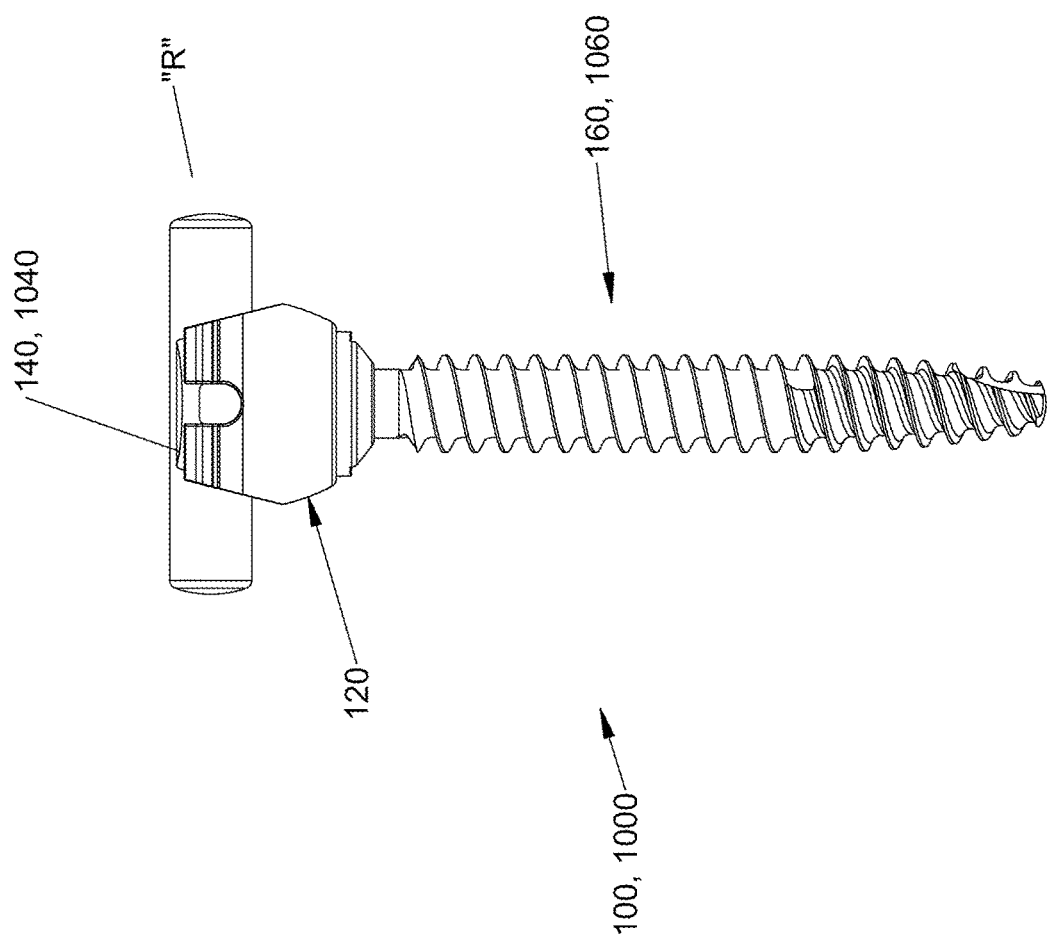
FIG. 14B is a side view of FIG. 14A with the spinal fixation device in a locked configuration.

When coupling spinal rod "R" to spinal fixation device 100, a portion of spinal rod "R" is positioned in a slot 142 of inner housing 140 and a corresponding slot 124 of outer housing 140 while dual layered housing 110 is in the unlocked configuration (FIG. 14A). Slots 142, 124 of inner and outer housings 140, 120, respectively, are configured and dimensioned to accommodate the geometry of spinal rod "R", and to retain spinal rod "R" therein without impairing the locking ability of spinal fixation device 100. Specifically, inner walls that define slot 142 impart a compressive force to an outer surface of spinal rod "R" which serves to securely hold and lock spinal rod "R" in its relative position with respect to inner housing 142. This required force is provided by the operational engagement of the locking device (not shown) with spinal fixation device 100 which results in the upward sliding motion of outer housing 120 relative to inner housing 140. A portion of spinal rod "R" is positioned in slot 142 and is secured therein when dual layered housing 110 is transitioned from the unlocked configuration (FIG. 14A) into the locked configuration (FIG. 14B). In the unlocked configuration, a gap "G" (FIG. 4) is defined between a top surface 143 of inner housing 140 and a top surface 123 of outer housing 120. As dual layered housing 110 is transitioned into the locked configuration, gap "G" is reduced. In an embodiment, gap "G" may be completely diminished in the locked configuration, such that the top surface 143 of inner housing 140 is substantially flush with the top surface 123 of outer housing 120 (FIG. 5).

In the locked configuration, spherical screw head 162 and spinal rod "R" may be securely fixed within dual layered housing 110. In the unlocked configuration, spherical screw head 162 may freely articulate within dual layered housing 110, and spinal rod "R" may be inserted or removed from dual layered housing 110. It is further envisioned that the taper lock configuration advantageously permits partial locking of dual layered housing 110, such that spinal rod "R" and spherical screw head 162 are partially secured therein permitting fine adjustments to be made prior to final locking. When partially locked, spherical screw head 162 may still rotate or pivot and spinal rod "R" may slide within slots 142, 124 of inner and outer housings 140, 120, respectively, transverse to the longitudinal axis "B" of dual layered housing 110. It should be appreciated that when partially locked spinal rod "R" is prevented from moving along the longitudinal axis "B" of dual layered housing 110, such that spinal rod "R" is prevented from being lifted out of slots 142, 124.

It should be appreciated that when coupled to the dual layered housing 110 the screw shaft 160 may rotate about the longitudinal axis "L" of screw shaft 160 and/or pivot about spherical screw head 162 in the unlocked, or partially locked, configurations. More specifically, screw shaft 160 may freely rotate about longitudinal axis "L" of screw shaft 160, and may further pivot about spherical screw head 162 relative to the longitudinal axis "B" of dual layered housing 110, such that a pivot angle is defined between longitudinal axis "L" of screw shaft 160 and the longitudinal axis "B" of dual layered housing 110. As screw shaft 160 pivots about spherical screw head 162, an advantageous pivot angle is achieved between the longitudinal axis "L" of screw shaft 160 and the longitudinal axis "B" of dual layered housing 110 (discussed below). As seen in FIG. 1, the longitudinal axis "L" of screw shaft 160 is substantially aligned with the longitudinal axis "B" of dual layered housing 110 such that the pivot angle is at or near zero.

Figure 5:
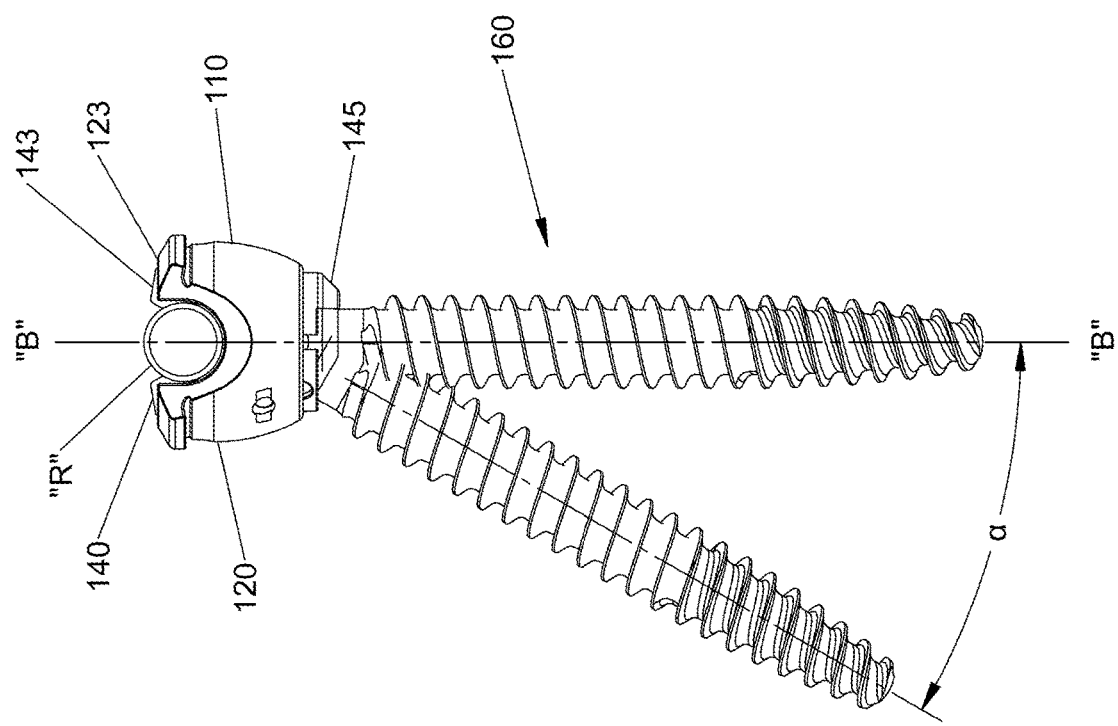
FIG. 5 is a front view of the spinal fixation device of FIG. 1 with a spinal rod, depicting a medial-lateral angle α.
Figure 6:
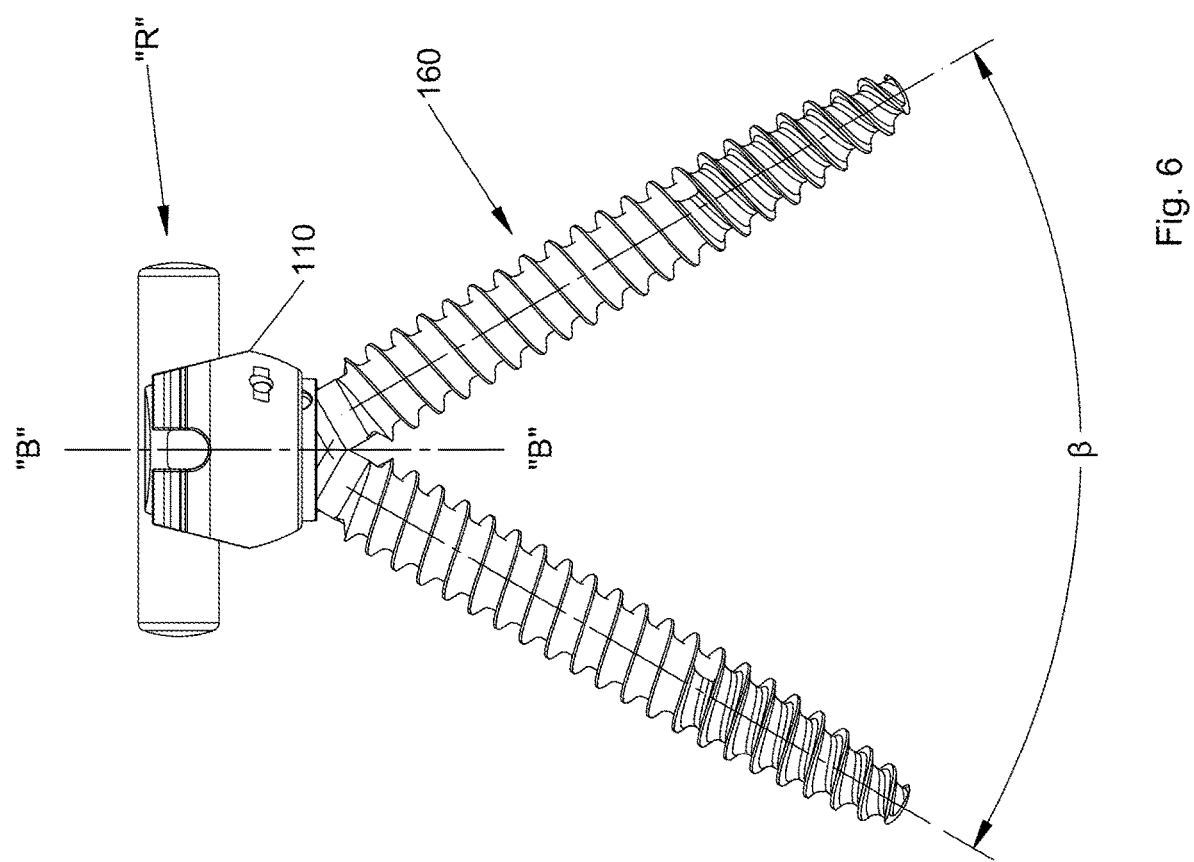
FIG. 6 is a side view of the spinal fixation device and spinal rod of FIG. 5, depicting a cranial-caudal angle β.

With reference to FIGS. 4-6, the pivotal relationship of dual layered housing 110 and screw shaft 160 will be further described. In use, contact surface 145 inhibits the pivoting of screw shaft 160 relative to dual layered housing 110 in the direction of contact surface 145, while permitting free pivoting motion in the directions opposing contact surface 145. Pivoting movement is limited in the direction of contact surface 145 by the engagement of the neck 166 of screw shaft 160 with the contact surface 145 of inner housing 140. More specifically, when spherical screw head 162 pivots with respect to dual layered housing 110 in the direction of contact surface 145, the neck 166 of screw shaft 160 comes into abutment with contact surface 145, thereby inhibiting screw shaft 160 from pivoting any further in the direction of contact surface 145, while simultaneously permitting screw shaft 160 to freely pivot in all other angular directions. It should be appreciated that during the pivoting of screw shaft 160, neck 166 fails to abut the distal surface 147 of inner housing 140, providing an increased degree of pivoting in directions opposite of contact surface 145, but when pivoted in the direction of contact surface 145 neck 166 comes into abutment therewith, thereby inhibiting any further pivoting in the direction of contact surface 145.

As shown in FIG. 5, the degree of pivoting of screw shaft 160 away from contact surface 145 is illustrated. It is envisioned that screw shaft 160 may pivot approximately up to about 60 degrees off of the longitudinal axis "B" of dual layered housing 110, as shown by pivot angle "α" (FIG. 5). It should be appreciated that traditional polyaxial pedicle screws known in the art typically maintain an angle of pivot of no more than 35 degrees. As shown, contact surface 145 inhibits the screw shaft 160 from pivoting past the longitudinal axis "B" in the direction of contact surface 145. With reference to FIG. 6, screw shaft 160 is uninhibited by contact surface 145 and may freely pivot an angle "β", such that angle "β" is transverse to contact surface 145. Accordingly, if contact surface 145 is configured to inhibit screw shaft 160 from pivoting in the medial-lateral direction for example, screw shaft 160 may still freely pivot in the cranial-caudal direction.

It should be appreciated that since dual layered housing 100 may rotate about longitudinal axis "L" of screw shaft 160, contact surface 145 of inner housing 140 may be oriented in any direction about the longitudinal axis "L". As such, when adjusting dual layered housing 100, the direction of contact surface 145 may be oriented to inhibit screw shaft 160 from pivoting in any direction incrementally located 360 degrees about the longitudinal axis "L" of screw shaft 160.

It is further envisioned that contact surface 145 may be configured to inhibit a larger or smaller pivot angle "a". As such, contact surface 145 may extend distally from the distal surface 147 of inner hosing 140 a longer or shorter length, or may alternatively be disposed a longer or shorter distance along the circumference of the distal surface 147 of inner housing 140. In this manner, screw shaft 160 may be inhibited from pivoting relative to dual layered housing 110 by contact surface 145 in all but a narrow angular range or in a single direction.

In accordance with the present disclosure an alternate embodiment of a bone screw will now be described with reference to FIGS. 7-12, and is generally designated as spinal fixation device 1000. Spinal fixation device 1000 includes dual layered housing 1010, screw shaft 1060, and a protuberance 900. It should be appreciated that dual layered housing 1010 and screw shaft 1060 are substantially similar to dual layered housing 110 and screw shaft 160 as discussed above, wherein distinctions and differences will be discussed below. Further, the locking and unlocking configurations of dual layered housing 1010, with respect to screw shaft 1060 and spinal rod "R", operate substantially similar to dual layered housing 110, and therefore will be omitted for brevity.

Figure 7:
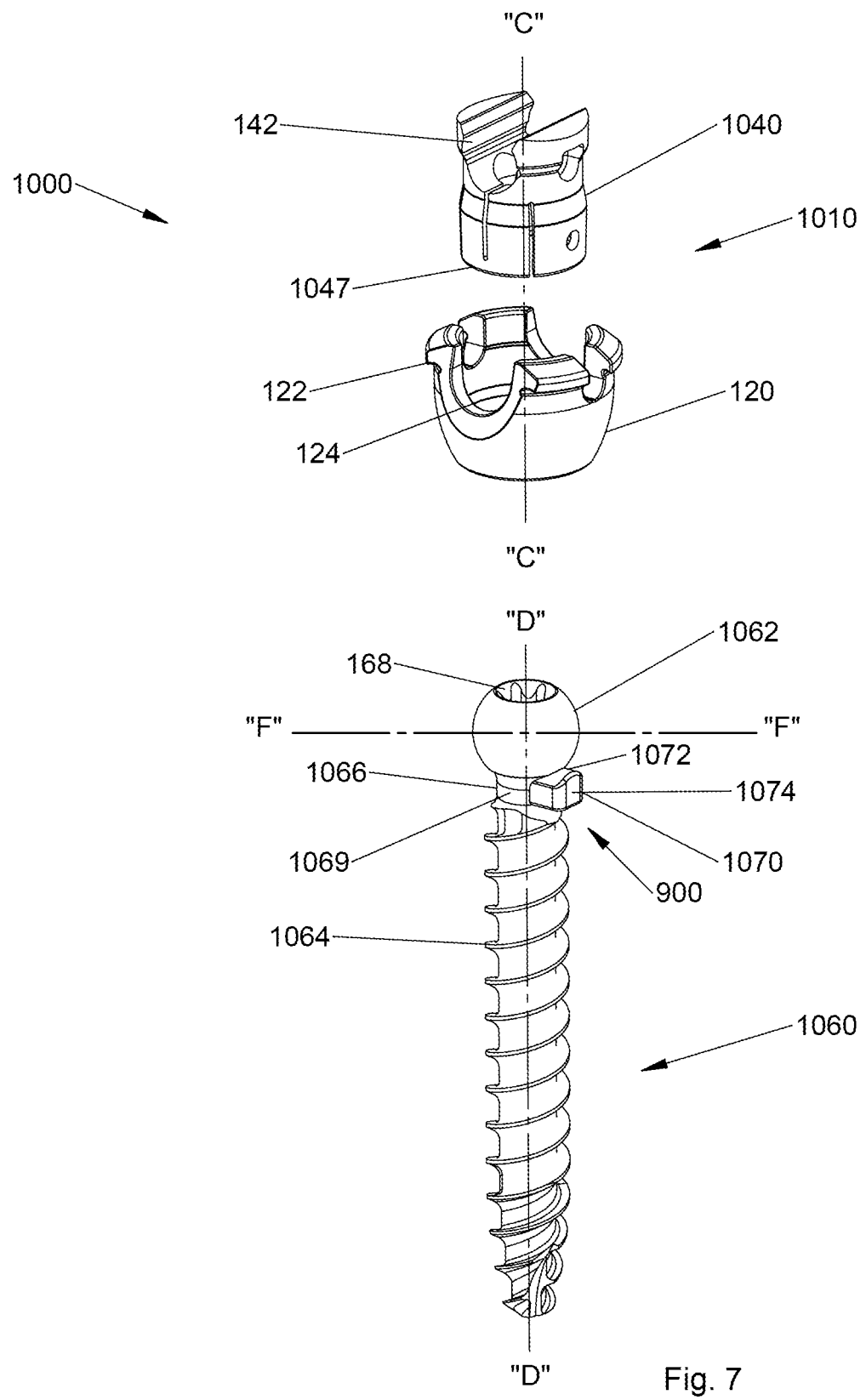
FIG. 7 is a front perspective view, with parts separated, of a spinal fixation device in accordance with another embodiment of the present disclosure.
Figure 8:
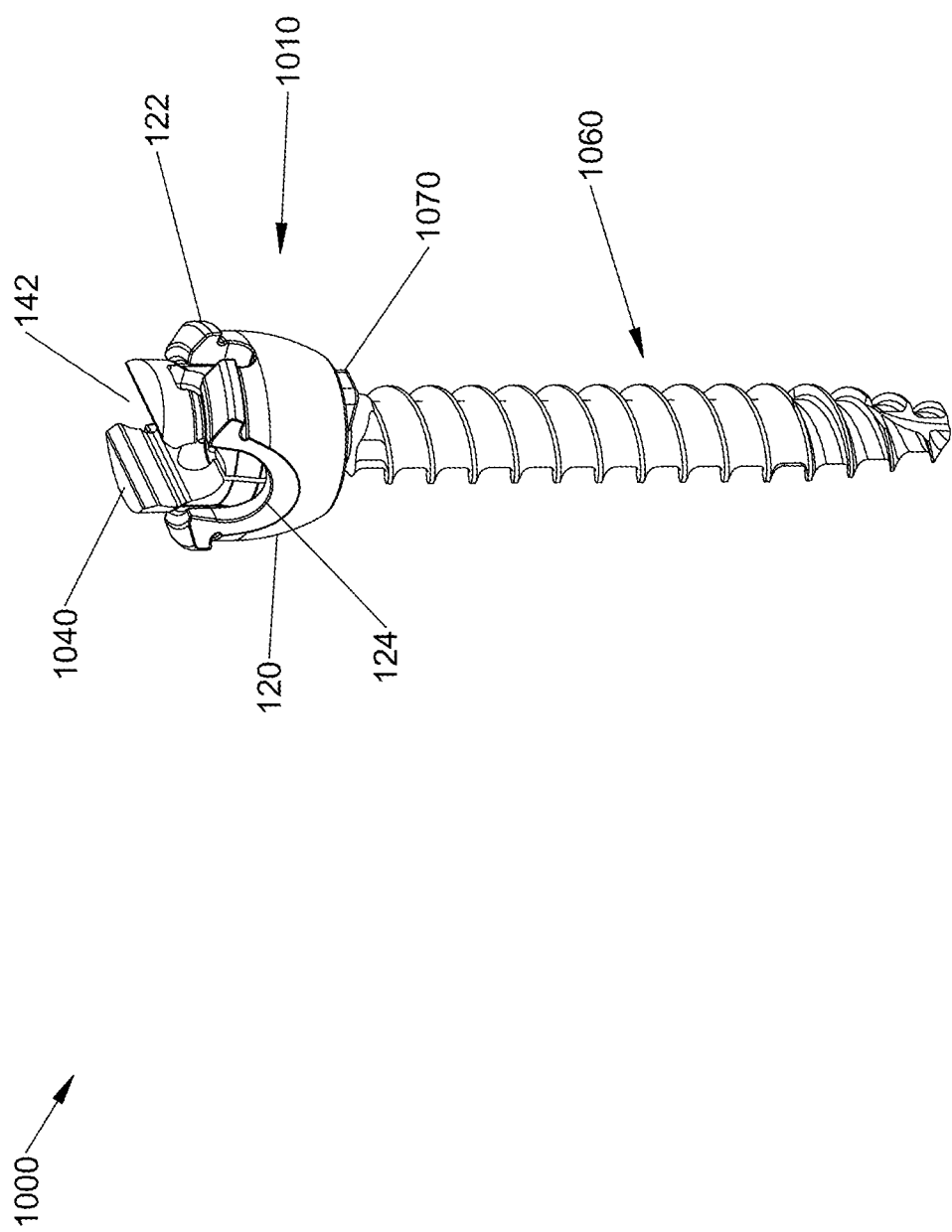
FIG. 8 is a front perspective view, with parts assembled, of the spinal fixation device of FIG. 7.

As illustrated in FIGS. 7 and 8, the inner housing 1040 of dual layered housing 1010 includes a distal surface 1047 which is generally planar, without a contact surface extending therefrom. Similarly to screw shaft 160, screw shaft 1060 includes a spherical screw head 1062, a threaded distal portion 1064, a neck portion 1066 therebetween, and an equator "F" being transverse to a longitudinal axis "D" of screw shaft 1060. It is envisioned that neck 1066 may be generally circular having an outer surface 1069 along its circumference. Screw shaft 1060 further includes protuberance 900 as a protrusion 1070 extending radially outward from the outer surface 1069 of neck portion 1066 along a portion of the circumference, such that protrusion 1070 is adapted to abut a portion of dual layered housing 1010 when coupled. More particularly, with screw shaft 1060 coupled to dual layered housing 1010, a top surface 1072 of protrusion 1070 abuts a portion of distal surface 1047 of inner housing 1040 (FIG. 10).

Figure 10:
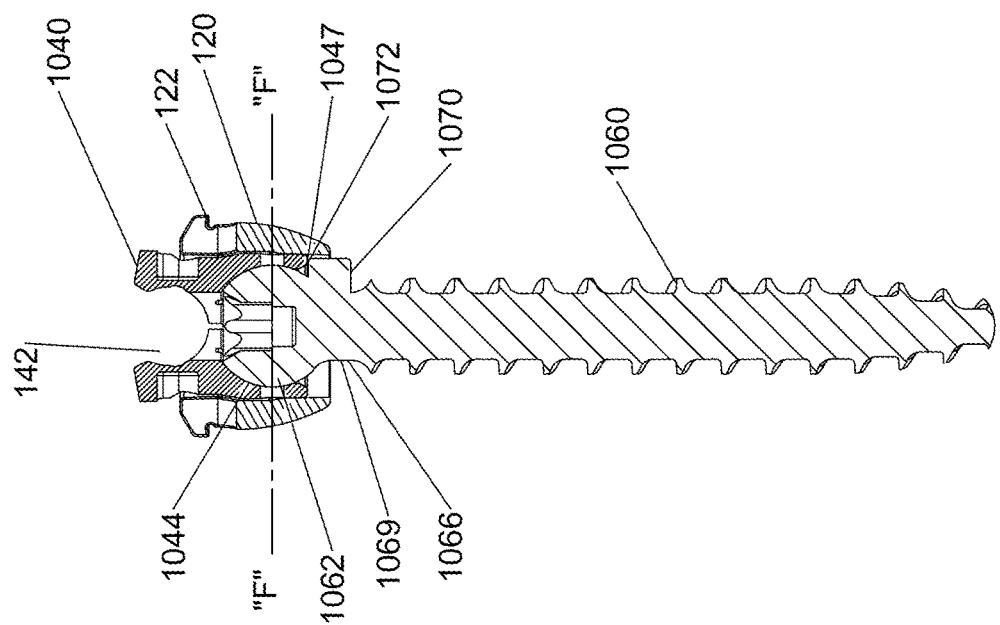
FIG. 10 is a cross-sectional view, taken along section line 10-10 of FIG. 9, of the spinal fixation device of FIG. 7.
Figure 9:
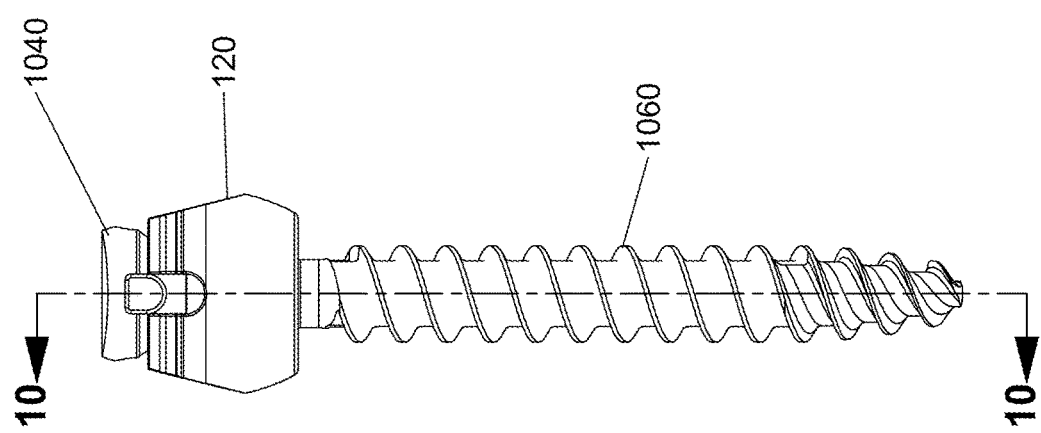
FIG. 9 is a side view of the spinal fixation device of FIG. 7.

With reference to FIGS. 10-12, the rotational and pivotal relationship of dual layered housing 1010 and screw shaft 1060 will be further described. It should be appreciated that dual layered housing 1010 can freely rotate about the longitudinal axis "D" of screw shaft 1060, and further, protrusion 1070 limits pivoting of screw shaft 1060 with respect to dual layered housing 1010 in a similar fashion as contact surface 145 of spinal fixation device 100. In use, protrusion 1070 inhibits a pivot angle of screw shaft 1060 relative to dual layered housing 1010 in the direction of protrusion 1070, while permitting free pivoting in all direction opposing protrusion 1070. More specifically, when spherical screw head 1062 pivots with respect to dual layered housing 1010, the protrusion 1070 of screw shaft 1060 comes into abutment with the distal surface 1047 of inner housing 1040 (FIG. 10), thereby inhibiting screw shaft 1060 from pivoting in the direction of protrusion 1070, while permitting screw shaft 1060 to freely pivot in all other angular directions. It should be appreciated that during the pivoting of screw shaft 1060, neck 1066 fails to abut the distal surface 1047 of inner housing 1040, which provides an increased degree of pivoting in directions opposite of protrusion 1070.

As shown in FIG. 11, the degree of pivoting of screw shaft 1060 away from protrusion 1070 is illustrated. It is envisioned that screw shaft 1060 may pivot approximately up to about 60 degrees relative to a longitudinal axis "C" of dual layered housing 1010, as shown by pivot angle "θ" (FIGS. 7 and 11). As shown, protrusion 1070 inhibits the screw shaft 1060 from pivoting past the longitudinal axis "C" in the direction of protrusion 1070. With reference to FIG. 12, screw shaft 1060 is uninhibited by protrusion 1070 and may freely pivot an angle "φ", such that pivot angle "y" is transverse to protrusion 1070. Accordingly, if protrusion 1070 is configured to inhibit pivoting of screw shaft 1060 in the medial-lateral direction, screw shaft 1060 may still pivot freely in the cranial-caudal direction.

It is further envisioned that the protrusion 1070 may be configured to inhibit a greater or smaller pivot angle "θ". As such, protrusion 1070 may extend radially from surface 1069 of neck 1066 a further or shorter distance, or may alternatively be disposed a longer or shorter distance along the circumference of the neck 1066. In this manner, screw shaft 1060 may be inhibited from pivoting relative to dual layered housing 1010 by protrusion 1070 in all but a narrow angular range or in a single direction.

It is further envisioned that dual layered housing 110 may be coupled to bone screw 1060, such that the resulting spinal stabilization device contains both the contact surface 145 of inner housing 140 and protrusion 1070 of bone screw 1060 to achieve a desired degree of inhibited pivoting of screw shaft 1060 with respect to dual layered housing 110.

Figure 13:
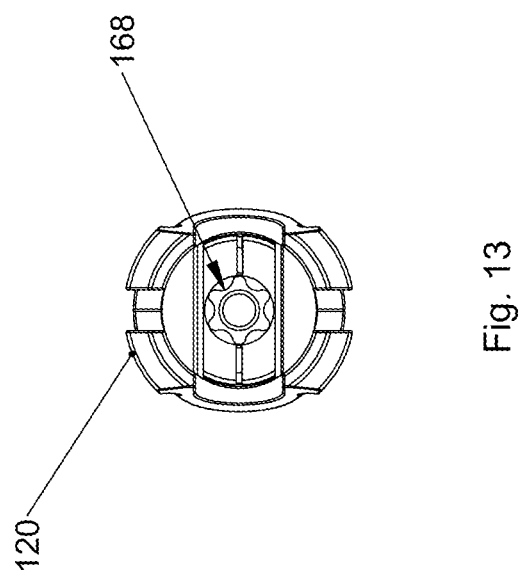
FIG. 13 is a top view of the spinal fixation device of FIGS. 1 and 7.

It is envisioned that spherical screw head 162, 1062 of bone screws 100, 1000, respectively, may further include a drive recess 168 disposed on a proximal end thereof (FIGS. 4, 10, and 13). Drive recess 168 is adapted to receive a drive tool (not shown) to facilitate the securement of the threaded distal portions 164, 1064 into bone. It is envisioned that drive recess 168 may accommodate a variety of drive types known in the art, e.g., hex socket, Philips, or slotted drive heads.

With reference to FIGS. 14A and 14B, the locked and unlocked configurations of dual layered housing 110, 1010 is illustrated. As discussed above, outer housing 120 can be selectively positioned relative to inner housings 140, 1040 of bone screws 100, 1000. With dual layered housing 110, 1010 in the unlocked configuration (FIG. 14A), spinal rod "R" is positioned in slots 142, 124 (FIG. 1) of inner housing 140, 1040 and outer housing 120. As outer housing 120 is driven upward towards inner housing 140, 1040 into the locked configuration (FIG. 14B), spinal rod "R" is securely fixed in slots 142, 124, and further, spherical screw head 162, 1062 (FIGS. 1 and 7) is securely fixed within inner housing 140, 1040.

With reference to FIGS. 1-14B, a method of performing spinal stabilization utilizing spinal fixation device 100 will be discussed. It should be appreciated that the below method may be performed with spinal fixation device 1000 in a similar fashion as spinal fixation device 100, therefore for the sake of brevity, the below method will only be described with reference to spinal fixation device 100. Further, the method may be performed utilizing a plurality of bone screws 100 or bone screws 1000, where bone screws 100, 1000 are implanted into sequential bones and a portion of spinal rod "R" is secured into each respective spinal fixation device 100, 1000 such that spinal rod "R" spans over multiple bones.

In use, a surgeon accesses the patient's spine in a known manner either using open surgical techniques or minimally invasive techniques, and prepares the bone to receive one or more bone screws 100, as is deemed appropriate under the circumstances. Spinal fixation device 100 is inserted into bone according to the operative plan of the surgeon, and spinal rod "R" is placed in or adjacent slots 142, 124 of inner and outer housings 140, 120 respectively. During operative plans making use of a plurality of bone screws 100, spinal rod "R" is positioned such that spinal rod "R" spans between adjacent bone screws 100.

The surgeon then uses a locking instrument (not shown) to transition dual layered housing 110 of each spinal fixation device 100 into the locked or partially lock configuration, such that spinal rod "R" is locked or partially locked therein. By first partially locking each spinal fixation device 100, the surgeon may advantageously readjust the orientation of spinal fixation device 100 and spinal rod "R" to better suit the surgical situation before transitioning dual layered housing 110 into the locked configuration.

More specifically, the orientation of dual layered housing 110 with respect to screw shaft 160, and/or a contour of spinal rod "R", may be adjusted while in the partially locked configuration. Once screw shaft 160 is implanted into bone, spinal rod "R" may be inserted into the slots 142, 124 of inner and outer housings 140, 120 respectively, and the locking instrument may be used to drive outer housing 120 proximally with respect to inner housing 140, towards the partially locked configuration. With dual layered housing 110 partially locked, dual layered housing 110 may be rotated about longitudinal axis "L" of screw shaft 160, or pivoted about spherical screw head 162, to a final angular orientation, and the position or contour of spinal rod "R" may be adjusted as desired. The surgeon will orient the inner and outer housings 140, 120 relative to the spherical screw head 162 such that the contact surface 145 is oriented to selectively inhibit screw shaft 160 from pivoting in the direction of contact surface 145. It is envisioned that the surgeon may initially orient the inner and outer housings 140, 120 relative to the spherical screw head 162 while in the unlocked configuration, and/or may perform an initial, or subsequent, orientation when the dual layered housing 110 is partially locked.

Spinal fixation device 100 advantageously permits spinal rod "R" to be adjusted during the procedure, and additional provides rotational and pivotal flexibility after implanting spinal fixation device 100 into bone, such that securing spinal rod "R" within dual layered housing 110 may be more easily accomplished. It has been found that by partially locking spinal fixation device 100, and readjusting the orientation of spinal fixation device 100 and the position or contour of spinal rod "R" during the procedure, the surgeon obtains superior surgical results. That is, with prior screws and rods, if the surgeon attempted to partially lock the screws, i.e., partially tighten the screw or nut, and then to readjust the construct, the construct under the forces exerted by the anatomy would not remain in position to allow the surgeon to return to tighten and lock the screws. With spinal fixation device 100, the surgeon may partially lock spinal fixation device 100 so that as subsequent adjusts are made to the orientation of spinal fixation device 100 and spinal rod "R" the construct will stay in the adjusted position. The partial locked position of spinal fixation device 100 thus provides great flexibility to the surgeon in making any adjustments deemed necessary such as, but not limited to, the rotation or pivoting of dual layered housing 110, or compression, distraction, or rotation of the entire construct or of individual bodies associated with spinal fixation device 100.

After completing whatever adjustments are required, the surgeon can then fully lock each spinal fixation device 100 with the locking instrument. This technique is particularly advantageous for deformity cases, where long constructs need to be adjusted during surgery in order to obtain the best clinical results. With continued use of the locking instrument, outer housing 140 may be driven to the proximal most position with respect to inner housing 120, thereby locking the orientation of dual layered housing 110 with respect to screw shaft 160, and further lock a portion of spinal rod "R" within the dual layered housing 110 of each respective spinal fixation device 100.

A kit for performing spinal stabilization utilizing spinal fixation device 100 will now be discussed with reference to FIGS. 1-14B. The kit may include at least one spinal fixation device 100 and at least one spinal rod "R". It is further envisioned that the kit may include a plurality of bone screws 100, a plurality of spinal rods "R" of varying dimensions, and a plurality of spinal rods "R" of varying materials, or any combination thereof. Further, the kit may include rod bending devices and/or rod reduction devices as discussed above. It should be appreciated that the kit may alternatively, or additionally, include spinal fixation device 1000 or a plurality of spinal fixation devices 1000.

Although the illustrative embodiments of the present disclosure have been described herein with reference to the accompanying drawings, the above description, disclosure, and figures should not be construed as limiting, but merely as exemplifications of particular embodiments. One skilled in the art will recognize that the present disclosure is not limited to use in spine surgery, and that the instrument and methods can be adapted for use with any suitable surgical device. It is to be understood, therefore, that the disclosure is not limited to those precise embodiments, and that various other changes and modifications may be effected therein by one skilled in the art without departing from the scope or spirit of the disclosure.

What is claimed is:

1. A spinal fixation device comprising:
   an inner housing;
   an outer housing circumferentially disposed around at least a portion of the inner housing, wherein the outer and inner housings are translatable relative to one another to transition the spinal fixation device between a locked configuration and an unlocked configuration;
   a screw including a screw head pivotably coupled to a lower portion of the inner housing and a shaft extending from the screw head, the screw including a neck disposed between the screw head and the shaft; and
   a pivot inhibitor disposed along an outer surface of the neck of the screw, such that pivoting of the screw relative to the inner housing is inhibited in a direction of the pivot inhibitor past a central longitudinal axis defined by the inner housing.

2. The spinal fixation device of claim 1, wherein the pivot inhibitor extends radially outward from the outer surface of the neck.

3. The spinal fixation device of claim 2, wherein the pivot inhibitor extends radially outward further than a radially outer dimension of each of the screw head and the shaft.

4. The spinal fixation device of claim 1, wherein the pivot inhibitor is monolithically formed with the screw.

5. The spinal fixation device of claim 1, wherein the pivot inhibitor further includes a top surface and the inner housing further includes a distal surface, and wherein the top surface abuts the distal surface when a longitudinal axis of the shaft is coaxial with a longitudinal axis of the inner housing.

6. The spinal fixation device of claim 5, wherein the distal surface of the inner housing is transverse to the longitudinal axis of the inner housing.

7. The spinal fixation device of claim 1, wherein the inner housing defines a slot therein, the slot configured to receive a portion of a spinal rod therein.

8. The spinal fixation device of claim 1, wherein at least one of the inner and outer housings is rotatable relative to the screw head about a longitudinal axis of the shaft.

9. The spinal fixation device of claim 1, wherein pivoting of the screw relative to the inner housing in a first direction is limited by the pivot inhibitor, and in a second direction is limited by a bottom surface of the outer housing, the second direction different from the first direction.

10. The spinal fixation device of claim 9, wherein the pivot inhibitor inhibits pivoting of the screw relative to the inner housing in a first plane, the first direction and second directions being along the first plane, the second direction being opposite to the first direction, and such that pivoting of the screw relative to the inner housing in a second plane transverse to the first plane is limited by the bottom surface of the outer housing in both a third direction and a fourth direction along the second plane, the fourth direction being opposite to the third direction.

11. The spinal fixation device of claim 10, wherein the screw is free to pivot relative to the inner housing across a first angular range in the first plane and a second angular range in the second plane.

12. The spinal fixation device of claim 11, wherein the first angular range and the second angular range are non-zero.

13. The spinal fixation device of claim 1, wherein the inner and outer housings define respective top surfaces, a gap between the top surfaces being greater in the unlocked configuration of the spinal fixation device than in the locked configuration of the spinal fixation device.

14. The spinal fixation device of claim 1, wherein the outer housing includes a pin extending radially inward and the inner housing includes a slot, the slot configured to receive the pin of the outer housing in sliding engagement such that rotational alignment between the inner housing and the outer housing is maintained.

15. The spinal fixation device of claim 1, wherein the screw head is prevented from pivoting within the inner housing in the locked configuration.

16. The spinal fixation device of claim 15, wherein the inner housing and the outer housing may arrive at a partially locked configuration between the unlocked configuration and the locked configuration, wherein, in the partially locked configuration, the outer housing compresses the inner housing onto the screw head while the screw head remains able to pivot relative to the inner housing.

17. A method of fixing a rod to a vertebra using the spinal fixation device of claim 16, the method comprising:
    driving the shaft into the vertebra;
    placing the rod within a slot defined within the inner housing while the inner housing and the outer housing are in the unlocked configuration;
    after placing the rod within the slot, pivotally adjusting the inner housing and the outer housing relative to the screw head while the inner housing and the outer housing are in the partially locked configuration; and
    after pivotally adjusting the inner housing and the outer housing relative to the screw head, transitioning the inner housing and the outer housing from the partially locked configuration to the locked configuration.

18. The method of claim 17, wherein driving the shaft into the vertebra includes driving the spinal fixation device to a final position wherein the pivot inhibitor is oriented such that it extends medially or laterally relative to the vertebra.

* * * * *